United States Patent
Bower et al.

(10) Patent No.: US 10,722,157 B2
(45) Date of Patent: Jul. 28, 2020

(54) APPARATUS AND METHOD FOR MONITORING BIOMETRIC PARAMETERS USING AN AMBIENT LIGHT COLLECTOR

(71) Applicant: Nokia Technologies Oy, Espoo (FI)

(72) Inventors: Chris Bower, Cambridge (GB); Michael Astley, Cambridge (GB); Piers Andrew, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 373 days.

(21) Appl. No.: 15/324,456

(22) PCT Filed: Jun. 12, 2015

(86) PCT No.: PCT/FI2015/050418
§ 371 (c)(1),
(2) Date: Jan. 6, 2017

(87) PCT Pub. No.: WO2016/005654
PCT Pub. Date: Jan. 14, 2016

(65) Prior Publication Data
US 2017/0156650 A1    Jun. 8, 2017

(30) Foreign Application Priority Data
Jul. 8, 2014   (GB) .................................. 1412076.0

(51) Int. Cl.
*A61B 5/1455*   (2006.01)
*A61B 5/024*    (2006.01)
*A61B 5/00*     (2006.01)

(52) U.S. Cl.
CPC ...... *A61B 5/14552* (2013.01); *A61B 5/02427* (2013.01); *A61B 5/6802* (2013.01);
(Continued)

(58) Field of Classification Search
CPC ............ A61B 5/02427; A61B 5/14552; A61B 5/6802; A61B 5/681; A61B 5/6833; A61B 2562/0233; A61B 2562/0238
See application file for complete search history.

(56) References Cited

U.S. PATENT DOCUMENTS

| | | | |
|---|---|---|---|
| 2011/0245637 A1* | 10/2011 | McKenna | A61B 5/14552 600/310 |
| 2012/0080613 A1* | 4/2012 | Kingsley | C09K 11/025 250/459.1 |

(Continued)

FOREIGN PATENT DOCUMENTS

| | | |
|---|---|---|
| CN | 201256969 Y | 6/2009 |
| CN | 103271743 A | 9/2013 |

(Continued)

OTHER PUBLICATIONS

International Search Report and Written Opinion received for corresponding Patent Cooperation Treaty Application No. PCT/FI2015/050418, dated Sep. 25, 2015, 9 pages.

*Primary Examiner* — Eric F Winakur
(74) *Attorney, Agent, or Firm* — Harrington & Smith (57) ABSTRACT

An apparatus and method, the apparatus comprising; a light collector configured to collect ambient light and provide the collected light to a portion of skin of a user; a photodetector configured to enable a biometric parameter to be monitored by detecting changes in the light absorbed by the portion of skin; and an amplifier configured to amplify an output signal provided by the photodetector; wherein the light collector is configured to filter the collected ambient light to increase the proportion of light within a selected range of wavelengths which is provided to the portion of skin of the user relative to the collected ambient light.

20 Claims, 4 Drawing Sheets (52) U.S. Cl.
CPC ............ *A61B 5/681* (2013.01); *A61B 5/6833* (2013.01); *A61B 2562/0233* (2013.01); *A61B 2562/0238* (2013.01)

(56) References Cited

U.S. PATENT DOCUMENTS

2015/0148633 A1    5/2015   Park
2015/0245637 A1    9/2015   Bocchini

FOREIGN PATENT DOCUMENTS

CN           102512178 B    4/2014
WO    WO-2009/153700 A1   12/2009

\* cited by examiner

APPARATUS AND METHOD FOR MONITORING BIOMETRIC PARAMETERS USING AN AMBIENT LIGHT COLLECTOR

RELATED APPLICATION

This application was originally filed as Patent Cooperation Treaty Application No. PCT/FI2015/050418 filed Jun. 12, 2015 which claims priority benefit to GB Patent Application No. 1412076.0, filed Jul. 8, 2014.

TECHNOLOGICAL FIELD

Examples of the disclosure relate to an apparatus and method for monitoring biometric parameters. In particular, they relate to an apparatus and method for monitoring biometric parameters by detecting changes in light absorbed or scattered by the skin or other body tissues of a user.

BACKGROUND

Electronic devices which may be positioned on or close to the body of a user to enable biometric parameters to be monitored are known. For example, devices which may be used to measure heart rate, blood oxygenation levels, temperature, galvanic skin conductance and other biometric parameters are known. These devices may comprise light sources which may be used to illuminate a portion of skin of the user. The biometric parameters can then be determined by monitoring the amount of light absorbed or scattered by the illuminated portion of skin.

It is useful to provide electronic devices which can be used to monitor biometric parameters for an extended period of time. This requires an electronic device which can be worn by a user for the extended period of time without causing discomfort to the user. It also requires that the electronic device has low power requirements so that a reliable output signal can be provided over the extended period of time.

BRIEF SUMMARY

According to various, but not necessarily all, examples of the disclosure, there may be provided an apparatus comprising; a light collector configured to collect ambient light and provide the collected light to a portion of skin of a user; a photodetector configured to enable a biometric parameter to be monitored by detecting changes in the light absorbed by the portion of skin; and an amplifier configured to amplify an output signal provided by the photodetector; wherein the light collector is configured to filter the collected ambient light to increase the proportion of light within a selected range of wavelengths which is provided to the portion of skin of the user relative to the collected ambient light.

In some examples the light collector may comprise a filter configured to allow light within a selected range of wavelengths to pass through.

In some examples the light collector may comprise photoluminescent material configured to absorb light of a first wavelength and reemit light within the selected range of wavelengths.

In some examples the light collector may be configured to filter for different selected ranges of wavelengths to enable different biometric parameters to be monitored.

In some examples the light collector may be configured to provide light in one range of wavelengths so that the apparatus can be used to monitor heart rate.

In some examples the light collector may be configured to provide light in two different ranges of wavelengths so that the apparatus can be used to monitor blood oxygenation levels.

In some examples the apparatus may comprise an array of photodetectors configured to enable a biometric parameter to be monitored by detecting changes in the light absorbed by the portion of skin.

In some examples the amplifier may be configured to provide a variable gain. The gain of the amplifier may be dependent upon the intensity of the ambient light.

In some examples the apparatus may comprise a further photodetector configured to detect the brightness of the ambient light.

In some examples the apparatus may comprise a supplementary light source. The supplementary light source may comprise one or more light emitting diodes.

In some examples the apparatus may be configured so that the light collector and photodetector may be positioned adjacent to the skin of the user.

In some examples the apparatus may be configured to be worn by a user.

According to various, but not necessarily all, examples of the disclosure, there may be provided a method comprising; providing a light collector configured to collect ambient light and provide the collected light to a portion of skin of a user; providing a photodetector configured enable a biometric parameter to be monitored by detecting changes in the light absorbed by the portion of skin; and providing an amplifier configured to amplify an output signal provided by the photodetector; wherein the light collector is configured to filter the collected ambient light to increase the proportion of light within a selected range of wavelengths which is provided to the portion of skin of the user relative to the collected ambient light.

In some examples the light collector may comprise a filter configured to allow light within a selected range of wavelengths to pass through.

In some examples the light collector may comprise photoluminescent material configured to absorb light of a first wavelength and reemit light within the selected range of wavelengths.

In some examples the light collector may be configured to filter for different selected ranges of wavelengths to enable different biometric parameters to be monitored.

In some examples the light collector may be configured to provide light in one range of wavelengths to enable a user's heart rate to be monitored.

In some examples the light collector may be configured to provide light in two different ranges of wavelengths to enable a user's blood oxygenation levels to be monitored.

In some examples the method may further comprise providing an array of photodetectors configured to enable a biometric parameter to be monitored by detecting changes in the light absorbed by the portion of skin.

In some examples the amplifier may be configured to provide a variable gain. The gain of the amplifier may be dependent upon the intensity of the ambient light.

In some examples the method may further comprise providing a further photodetector configured to detect the brightness of the ambient light.

In some examples the method may further comprise providing a supplementary light source. The supplementary light source may comprise one or more light emitting diodes.

In some examples the method may further comprise providing the light collector and photodetector adjacent to the skin of the user.

In some examples the light collector and detector may be provided in an apparatus configured to be worn by a user.

According to various, but not necessarily all, examples of the disclosure there may be provided examples as claimed in the appended claims.

BRIEF DESCRIPTION

For a better understanding of various examples that are useful for understanding the brief description, reference will now be made by way of example only to the accompanying drawings in which.

DETAILED DESCRIPTION

The Figures illustrate an apparatus 1 comprising; a light collector 3 configured to collect ambient light 13 and provide the collected light to a portion of skin 15 of a user; a photodetector 5 configured to enable a biometric parameter to be monitored by detecting changes in the light absorbed by the portion of skin 15; and an amplifier 7 configured to amplify an output signal 9 provided by the photodetector 5; wherein the light collector 3 is configured to filter the collected ambient light 13 to increase the proportion of light within a selected range of wavelengths which is provided to the portion of skin 15 of the user relative to the collected ambient light 13.

The apparatus 1 may be for monitoring a biometric parameter of a user. For example the apparatus 1 may be used to monitor heart rate, blood oxygenation levels or any other suitable parameter. The apparatus 1 may be configured to measure changes in the light absorbed by a sample volume 17 of skin 15 of the user due to changes in the volume of blood within the sample volume 17.

Figure 1:
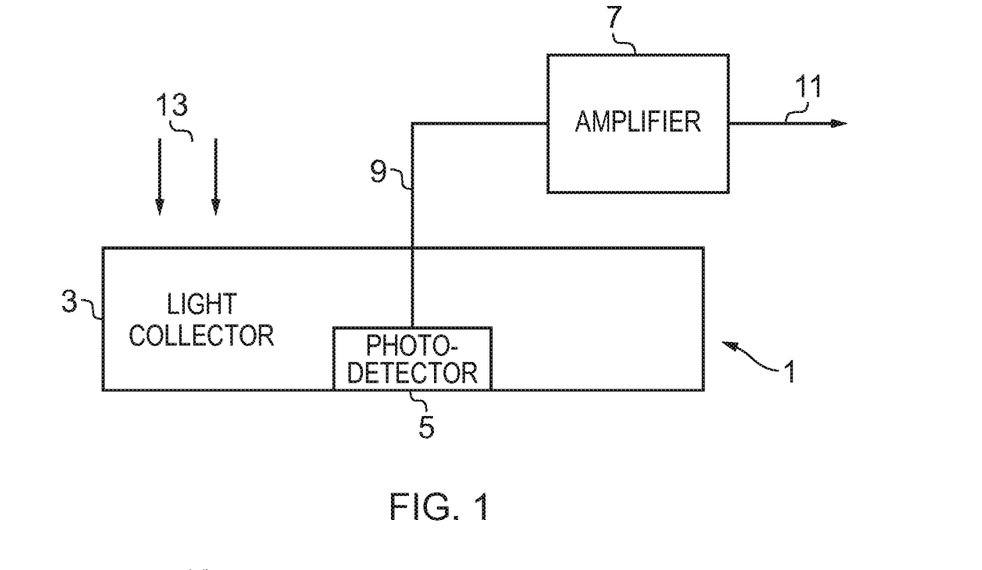
FIG. 1 illustrates an apparatus.

FIG. 1 schematically illustrates an apparatus 1 comprising a light collector 3 a photodetector 5 and an amplifier 7. The apparatus 1 may be configured to enable biometric parameters of a user to be measured. The apparatus 1 may be configured to enable ambient light 13 to be used as a probe signal to monitor the biometric parameters. Only features which have been referred to in the following description have been illustrated in FIG. 1. It is to be appreciated that in other examples the apparatus 1 may comprise other features. For example the apparatus 1 may comprise controlling circuitry which may be configured to control the amplifier 7. In some examples the apparatus 1 may comprise a transceiver which may enable the output signal 11 from the amplifier 7 to be read by a remote device.

The light collector 3 may comprise any means which may be configured to collect ambient light 13 and provide the collected light to a portion of skin of the user 15. The light collector 3 may comprise a wave guide or any other suitable means. The light collector 3 may be configured so that when the apparatus 1 is worn by the user the light collector 3 is positioned adjacent to a portion of skin 15 of the user. In some examples the light collector 3 may be configured so that when the apparatus 1 is worn by the user an outcoupling portion of the light collector 3 may be positioned adjacent to a portion of skin 15 of the user. This may enable the ambient light 13 collected by the light collector 3 to be provided to a portion of skin 15 of the user.

In other examples the apparatus 1 may be configured so that the light collector 3, or a portion of the light collector 3, may be located away from the skin 15 of the user. For example the light collector 3 may form part of a garment or textiles which may be worn. The garment or textile may be such that it extends over a larger area which may enable a greater amount of ambient light 13 to be harvested before the light is brought into contact with the skin 15 of the user in the desired measurement location.

The light collector 3 may be configured to increase the intensity of the light which is incident on the portion of skin 15 of the user relative to the intensity of the collected ambient light 13. For example the light collector 3 may comprise optical components which may be configured to focus the collected ambient light 13 onto a small area of the skin 15 of the user. The optical components may comprise any suitable means for focusing the collected ambient light 13 such as waveguides, lenses, micro-lenses, mirrors or any other suitable components.

In some examples the light collector 3 may be configured so that the area of skin 15 on which the collected light is focused may be small compared to the area over which the light collector 3 is configured to collect ambient light 13. This may increase the intensity of the light which is incident on the portion of skin 15 of the user relative to the intensity of the collected ambient light 13. As an example the light collector 3 may have a width of 20 mm and be configured to wrap around a wrist of the user. When the user has their arm in a horizontal position an area of approximately 20 mm by 60 mm may be configured to collect the ambient light 13. It is to be appreciated that this assumes a wrist diameter of 60 mm and that other dimensions may be used in other cases. The light collection area is therefore 1200 $mm^2$. The light collector 3 may be configured so that the collected ambient light 13 may be focused on an area of skin 15 of 10 mm by 10 mm. This may provide a large increase in the intensity of light which is used to illuminate the portion of skin 15 of the user.

In some examples the light collector 3 may be configured to filter the collected ambient light 13. In some examples the light collector 3 may be configured to spectrally filter the collected ambient light 13 to increase the proportion of light within a selected range of wavelengths which is provided to the skin 15 of the user relative to the collected ambient light 13. By increasing the intensity of light with wavelengths in the range of interest, the signal-to-noise ratio in the light collected by the photodetector 5 is increased.

In some examples the light collector 3 may comprise one or more filters which may be configured to spectrally filter the collected ambient light 13. The filter may comprise diffraction gratings, dichroic filters, dichroic mirrors or any other suitable means. The filters may be configured to allow light within one or more selected ranges of wavelengths to pass through. The filters may be configured to prevent light which is not in the one or more selected range of wavelengths from passing through.

In some examples the light collector 3 may be configured to filter the ambient light 13 by converting light which is in an unwanted range of wavelengths into light which is in a selected range of wavelengths. For example the light collector 3 may comprise photoluminescent material which may be configured to absorb light at a first range of wavelengths and reemit light in a second range of wavelengths. The first range of wavelengths may comprise an unwanted and/or harmful range of wavelengths. The second range of wavelengths may comprise one or more selected ranges of wavelengths which may be used for the probe signal to illuminate the skin 15 of the user. Examples of suitable photoluminescent material may be either phosphorescent (phosphors) or fluorescent (fluorophores). Phosphors may consist of a host material doped with an activator. The activator may be metallic. Suitable examples of phosphors comprise, but are not limited to, metal-doped: zinc oxide, zinc sulphide, magnesium fluoride, zinc silicate, yttrium silicate, yttrium oxide, yttrium oxide sulphide, indium borate, calcium sulfide, calcium silicate, calcium tungstate, magnesium tungstate, strontium aluminate, strontium phosphate and lanthanum phosphate. Iridium and platinum chelates may also be suitable. Suitable fluorescent materials comprise, but are not limited to (i) natural compounds such as quinine, chlorophyll, thiamine, niacin and riboflavin; (ii) laser dyes such as the coumarins (typically green-emitting), xanthenes including the fluoresceins and rhodamines (yellow/red-emitting) and cyanines; (iii) fluorescent conjugated polymers such as the polyfluorenes and poly(p-phenylene vinylene)s; (iv) organometallic chelates such as tris(8-hydroxyquinolinato)aluminium and rare-earth chelates, particularly terbium- and europium-chelates (green and red-emitting respectively) and (v) semiconductor quantum dots or nanocrystals. In some examples the photoluminescent material may be configured to absorb light in the ultra-violet (UV) range of the spectrum and reemit green light which may be used to monitor the heart rate of the user. In some examples the photoluminescent material may be configured to absorb light in the ultra-violet (UV) range of the spectrum and reemit red light which may be used to monitor the blood oxygenation of the user. This helps to remove unwanted and potentially harmful wavelengths of light and also increases the signal to noise ratio of the light which is detected by the photodetector 5.

In some examples the photoluminescent material may comprise brightening agents, though the reemission of brightening agents are typically blue rather than green. Examples of brightening agent materials comprises triazine-stilbenes, coumarins, imidazolines, diazoles, triazoles, benzoxazolines and biphenyl-stilbenes or any other suitable material.

In the example of FIG. 1 the light collector 3 is provided adjacent to a photodetector 5. The photodetector 5 may be positioned so that light which is scattered by the sample volume 17 of skin may be detected by the photodetector 5.

The photodetector 5 may comprise any means which may be configured to receive an input signal comprising electromagnetic radiation and convert this into an output signal 9. The photodetector 5 may be configured to convert light scattered by a sample volume 17 of skin 15 into an electrical output signal 9. This may enable changes in the amount of light absorbed by the sample volume 17 of skin 15 caused by changes in blood volume to be monitored. The output signal 9 may contain information relating to biometric parameters of a user of the apparatus 1.

The photodetector 5 may be a sensitive photodetector 5 and may be configured to detect low levels of incident light. In some examples the photodetector 5 may comprise a photodiode, a phototransistor, a light dependent resistor, a photodetector constructed with organic light sensitive materials, a graphene FET based photodetector or any other suitable means. In some examples the photodetector 5 may comprise highly sensitive material such as quantum dot material, semiconductor nanoparticles or any other material which is a strong absorber of light. The material used within the photodetector 5 may be selected to be optimised for light detection within the one or more selected wavelengths.

In some examples the apparatus 1 may comprise an array of photodetectors 5. The array of photodetectors 5 may comprise a plurality of photodetectors 5. Using an array of photodetectors 5 may improve the signal to noise ratio in the light collected by the array compared to the light collected by a single photodetector 5. Using an array of photodetectors 5 may also reduce the effects of motion based artefacts as a result of relative motion between the photodetector 5 and the skin 15 of the user.

The photodetector 5 or array of photodetectors 5 may be coupled to an amplifier 7. The output signal 9 from the photodetector 5 may be provided as an input signal to the amplifier 7. It is to be appreciated that the photodetector 5 and the amplifier may be operationally coupled and that any number of components may be provided between the amplifier 7 and the photodetector 5 including no intervening components.

Figure 3:
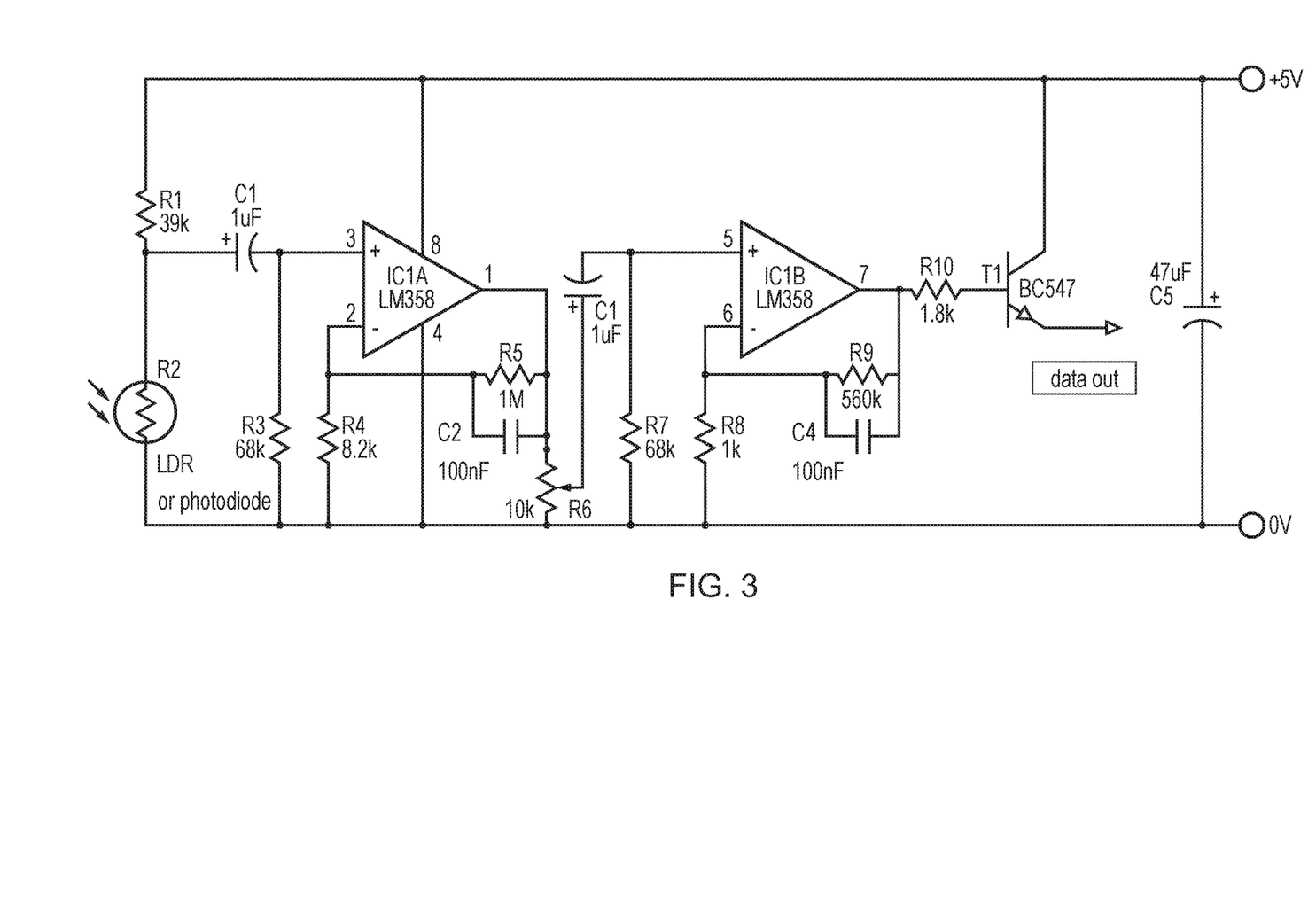
FIG. 3 illustrates an amplifier.

The amplifier 7 may comprise any means which may be configured to receive the output signal 9 from the photodetector 5 and amplify the signal 9 to provide an amplified output signal 11. The amplifier 7 may comprise a low power operational amplifier circuit. An example of an amplifier 7 is illustrated in FIG. 3.

The amplifier 7 may be arranged to provide a large gain. This may enable a very low power input signal 9 to be used to obtain a useful output signal 11. In some examples the gain provided by the amplifier 7 may be programmable. For example the gain may be programmed to be dependent upon the intensity of the ambient light 13. In such cases the gain provided by the amplifier 7 may be lower when the ambient light 13 has a high intensity and the gain may be higher when the ambient light 13 has a low intensity. This may enable the power consumption of the apparatus 1 to be minimised.

The output signal 11 provided by the amplifier 7 provides an indication of the amount of light within a selected range of wavelengths which has been absorbed or scattered by the skin 15 of the user. This may give an indication of biometric parameters such as the heart rate or blood oxygenation levels or any other suitable parameter. The output signal 11 may be provided to an output device, such as a display or other suitable device, so that a user can view the obtained information relating to the biometric parameters.

The apparatus 1 may be configured to be worn by a user. This may enable the photodetector 5 and the light collector 3 to be positioned adjacent to a portion of skin 15 of the user. In such examples the apparatus 1 may comprise means for attaching the apparatus 1 to a part of the body of the user. In some examples the light collector 3 may be provided within a strap so that the apparatus 1 can be fastened to a wrist or other suitable part of a user's body. In some examples the apparatus 1 may comprise adhesive portions so that the apparatus can be stuck to a part of the body of the user.

Figure 2:
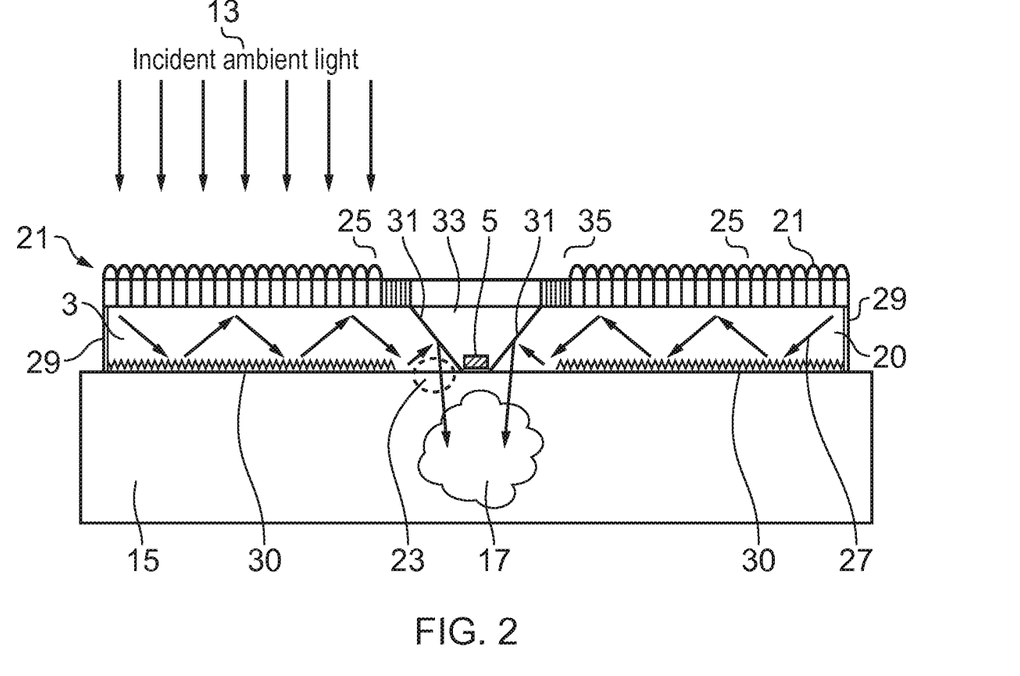
FIG. 2 illustrates an apparatus.

FIG. 2 illustrates a light collector 3 and a photodetector 5 which may be used within apparatus 1 in examples of the disclosure. In the example of FIG. 2 the light collector 3 and a photodetector 5 are illustrated in use positioned adjacent to a portion of skin 15 of the user. The light collector 3 is configured to illuminate a sample volume 17 of the skin 15. The photodetector 5 is positioned to detect light scattered by the sample volume 17 of skin 15

In the example of FIG. 2 the light collector 3 comprises an optical waveguide 20. The optical waveguide 20 may be configured to be held in position adjacent to the skin 15. The optical waveguide 20 may be configured so held in position so that at least a portion of the optical waveguide is in contact with the skin 15. This may ensure good optical contact of both the light collector 3 and the photodetector 5 with the surface of the skin.

The optical waveguide 20 may also be secured to the skin so as to minimize movement of the light collector 3 and/or photodetector 5 relative to the skin 15. This may help to ensure that the same sample volume 17 is being measured. In some examples the waveguide 20 may form a strap, such as a wrist strap or any other suitable means for attaching an apparatus 1 to the body of a user.

In some examples the optical waveguide 20 may be made of an elastomeric material. This may reduce the movement of the waveguide 20 and ensure that the apparatus 1 is comfortable for a user to wear.

The waveguide 20 may be manufactured using any suitable means such as moulding, embossing, imprinting or any other suitable means.

The light collector 3 comprises an incoupling region 21 and an outcoupling region 23. The incoupling region 21 is configured to couple incident ambient light 13 into the light collector 3. In the example of FIG. 2 incident ambient light 13 is only illustrated on one side of the light collector 3 however it is to be appreciated that it would be provided over the upper surface of the light collector 3.

The incoupling region 21 comprises a microlens array 25 coupled to the optical waveguide 20. The microlens array 25 may comprise a plurality of microlenses which be configured to concentrate the ambient light 13 into the waveguide 20. The microlens array 25 may comprise any means suitable for concentrating the ambient light 13.

The optical waveguide 20 may be configured to guide the collected light 27 towards the outcoupling portion 23. In the example of FIG. 2 the waveguide 20 comprises optical components which are configured to guide the collected light 27 towards the outcoupling portion 23. The optical components may be configured to optimise the amount of the collected light 27 which reaches the outcoupling portion 23 so as to focus the light on a small area of the user's skin.

In the example of FIG. 2 the optical waveguide comprises mirrors 29 at each end of the waveguide 20. The mirrors 29 may be configured so that light does not escape from the waveguide 20. The base of the waveguide 20 is patterned with a coupler microstructure 30. The coupler microstructure 30 is configured to scatter the cones of light focused by the microlens array 25. The cones of light are scattered laterally into the waveguide 20 to enable them to be guided through the waveguide 20 by total internal reflection. In some examples the coupler microstructure 30 may comprise an array of 120° apex prisms, which will direct the incoming light cone +/−60° with respect to the top surface of the waveguide 20.

The light collector 3 comprises means for directing incident light to the outcoupling portion 23 and into the sampling volume 17 of the skin 15 of the user. In the example of FIG. 2 the light collector 3 comprises additional mirrors 31 which are positioned adjacent to the photodetector 5. The additional mirrors 31 are angled to reflect incident collected light 27 through the outcoupling portion 23. In some examples the additional mirrors 31 may be non-planar. For instance the additional mirrors 31 may be paraboloidal. This may enable the additional mirrors 31 to focus the reflected light through the outcoupling region 23 into the sampling volume 17. Other components may be used in other examples of the disclosure. For example a diffraction grating may be provided on the base of the waveguide 20 in the outcoupling region 23 adjacent to the skin 15 of the user. The period of the diffraction grating may be tuned to direct light within a selected range of wavelengths into the sampling volume 17.

As mentioned above with reference to FIG. 1, the light collector 3 may be configured to filter the collected light 27. The filtering of the collected light 27 may increase the proportion of light within a selected range of wavelengths which is provided to the sample volume 17 of the user relative to the ambient light 13.

For example where the apparatus 1 is to be used to measure heart rate of a user it may be preferred to illuminate the sample volume 17 with green light. In such examples the filtering may be tuned to allow green light to pass though but to block other wavelengths of light. In other examples the apparatus 1 may be used to measure the blood oxygenation levels. In such examples it is preferred to alternately illuminate the sample volume 17 with both red light and infra-red light. In such examples the filtering may be tuned to allow red light and infrared light to pass though but to block other wavelengths of light. Time-gating of the light may be achieved by using an optical shutter or MEMS micro-mirror light switch or any other suitable means.

The filtering of the collected light 27 may be achieved using any suitable means. In some examples the mirrors 29, 31 may comprise dichroic filters so that the mirrors 29, 31 only reflect light within the selected ranges of wavelengths. In some examples the waveguide 20 may comprise one or more optical filters which may be configured to only allow light within the selected ranges of wavelengths to pass through. The optical filters may be provided between the microlens array 21 and the waveguide 20. In some examples the waveguide 20 may be formed from material which is configured to absorb unwanted wavelengths of light.

In other examples the filtering of the collected light may be achieved by using photoluminescent material which may absorb light at a first wavelength and reemit the light at a second wavelength. For example the photoluminescent material may absorb UV radiation which may be harmful to a user and convert this into useful green light that will further enhance a signal for monitoring heart rate. The photoluminescent material may be provided within the waveguide 20.

In some examples the apparatus 1 may be configured so that the light collector 3 is configured to filter for different ranges of wavelengths to enable different biometric parameters to be monitored. For instance the apparatus 1 may be tuned to filter for a first wavelength of light for a first period of time and a second wavelength of light for a second period of time. This may enable the same apparatus 1 to be used to measure different biometric parameters.

The photodetector 5 is provided in the center of the waveguide 20. In the example of FIG. 2 the photodetector 5 is surrounded with an opaque material 33. The opaque material may be configured to minimize illumination from light which has not been scattered from within the sampling volume 17 of skin 15.

In the example of FIG. 2 the light collector 3 comprises supplementary light sources 35. The supplementary light sources may comprise light emitting diodes (LEDs), organic light emitting diodes (OLEDs) or any other suitable means. The supplementary light sources 35 may be configured to enhance the ambient illumination and/or may be configured for use when the ambient light 13 falls below a given threshold.

In some examples the supplementary light sources 35 may be configured to be activated intermittently. This may enable high intensity illumination to be provided at regular intervals of time. This may be used to collect more detailed data relating to the biometric parameters and/or to ensure that the data obtained using the ambient light 13 is accurate.

In some examples the apparatus 1 may comprise a further photodetector. The further photodetector may be provided on an outer surface of the apparatus 1 and may be configured to enable the intensity of the ambient light 13 to be detected. The supplementary light sources 35 may be coupled to the further photodetector so that, if it is determined that the ambient light 13 is below a threshold level the supplementary light sources 35 may be activated. If is determined that the ambient light 13 is above a threshold level the supplementary light sources 35 may be deactivated. This may enable the apparatus 1 to be used at night time and in other occasions when the ambient light levels are low. This may provide for an efficient apparatus 1 as the supplementary light sources 35 are only activated when they are needed.

FIG. 3 illustrates an example amplifier 7 which may be used in examples of the disclosure. The amplifier 7 may be configured to provide a large gain so that a low power input signal can be converted into a useful output signal. In the example of FIG. 3 the amplifier 7 has up to 80 dB gain and a passband centered at 2.5 Hz with a 40 dB/decade roll off on either side. In the example of FIG. 3 the open loop gain of the amplifier 7 is much larger than the closed loop gain.

The amplifier 7 may be connected to a controlling circuitry which may allow the output signal 11 to be digitized.

In some examples the amplifier 7 may be configured to provide a variable gain. For instance, the static resistors R5 and R9 may be replaced with variable resistors such as digital potentiometers or field effect transistors (FETs) operating within the linear regime. A further photodetector may be configured to enable control of the variable resistors. The further photodetector may be provided on an external surface of the apparatus 1 and may be configured to measure the intensity of in the incident ambient light 13. Control circuitry such as a microcontroller with a look-up table may be used to convert the reading from the further photodetector to an appropriate feedback value. This may enable the gain of the amplifier 7 to be optimized to reduce power consumption. For example the amplifier 7 may be controlled to provide a larger gain in lower light conditions but to provide a smaller gain in bright light conditions. In some examples the same photodetector may be used to control supplementary light sources 35 and the amplifier 7.

It is to be appreciated that other means for controlling the gain of the amplifier 7 may be used in other examples of the disclosure. For example the programmable gain of the amplifier 7 may be controlled using digital potentiometers attached to a programming pin of the operational amplifier or any other suitable means.

Figure 4:
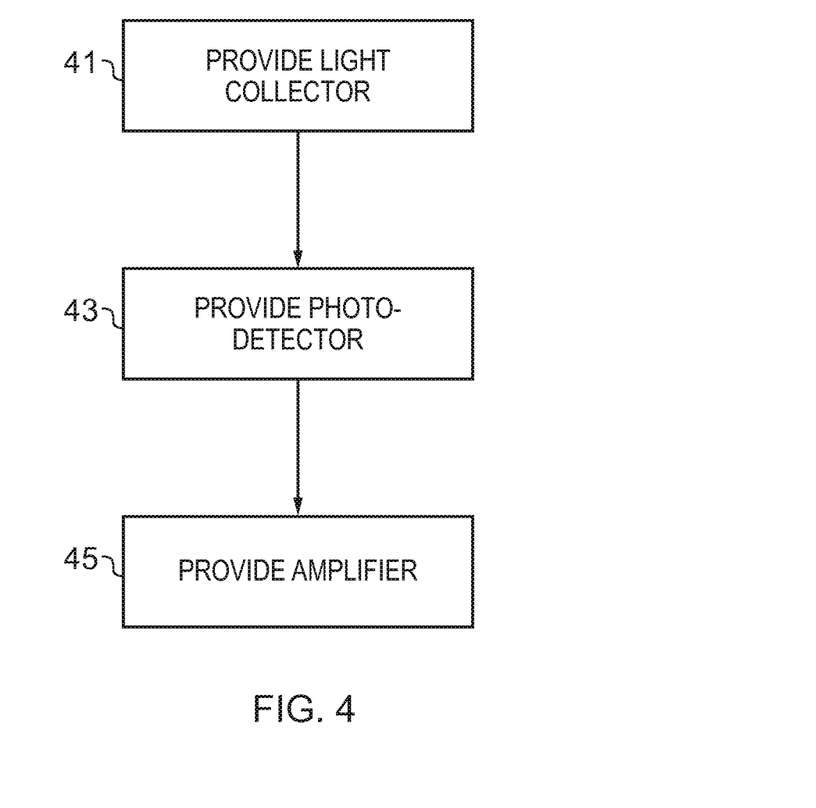
FIG. 4 illustrates a method.

FIG. 4 illustrates a method. The method of FIG. 4 may be used to provide an apparatus 1 as described above with reference to FIGS. 1 to 3. The method comprises, at block 41, providing a light collector 3 configured to collect ambient light 13 and provide the collected light to a portion of skin 15 of a user. At block 43 the method comprises providing a photodetector 5. The photodetector 5 is configured to detect changes in the light absorbed by the portion of skin 15. At block 45 the method comprises providing an amplifier 7 configured to amplify an output signal provided by the photodetector 5. The light collector 3 is configured to filter the collected ambient light 13 to increase the proportion of light within a selected range of wavelengths which is provided to the portion of skin 15 of the user relative to the collected ambient light.

Figure 5:
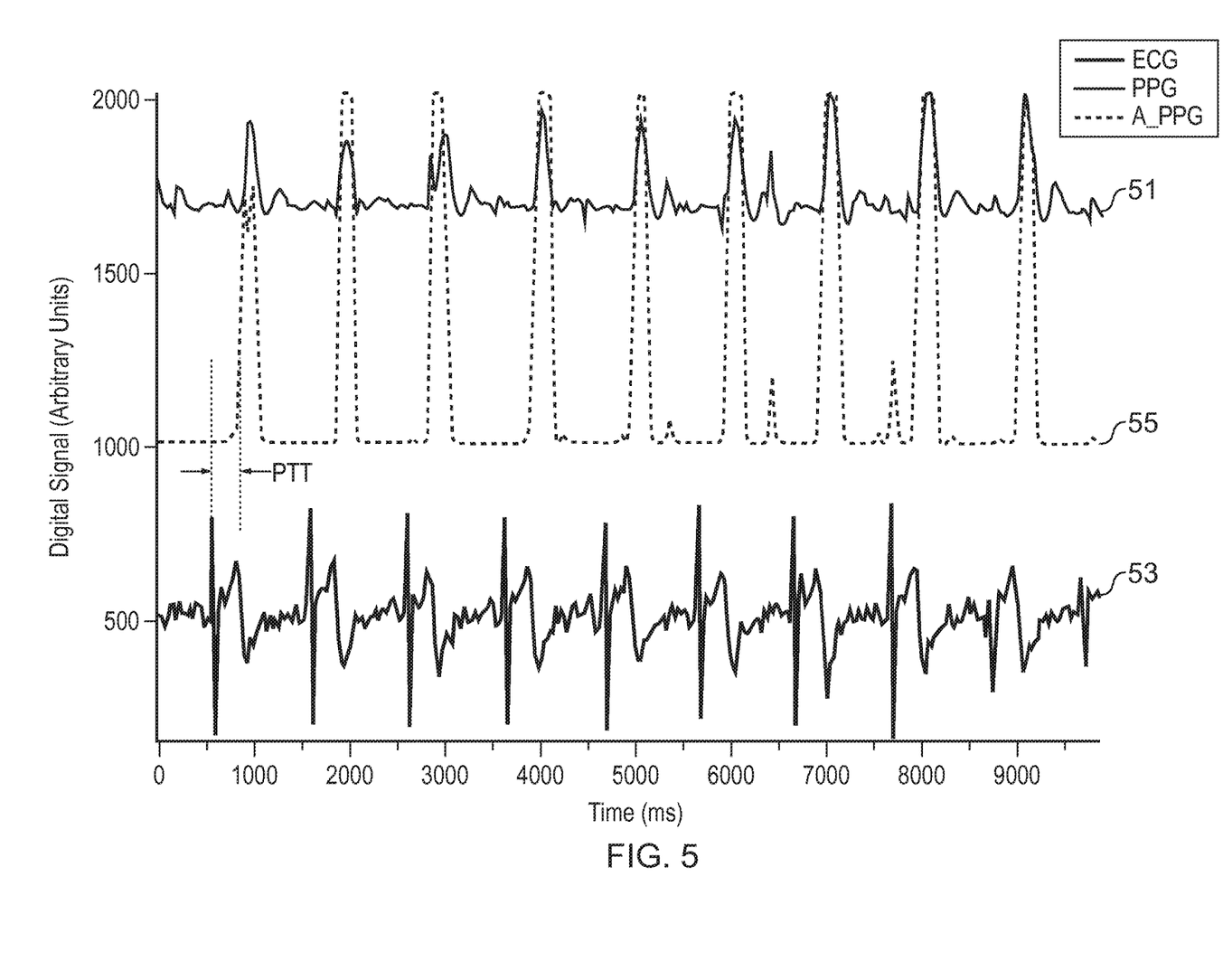
FIG. 5 illustrates results obtained with an example apparatus.

FIG. 5 illustrates results obtained using an example apparatus 1 to monitor heart rate.

Trace 51 comprises results obtained with a prior art photoplethsythmograph (PPG) which uses a green LED to illuminate the skin. Trace 53 comprises results obtained with an electrocardiogram (ECG) and trace 55 comprises results obtained with an apparatus 1 as described above with reference to FIGS. 1 to 3.

To obtain the results an example apparatus 1 was attached to a wrist of a user. No supplementary light sources 35 were used. An amplifier as illustrated in FIG. 3 was connected to the photodetector 5. The variable resistor R6 was adjusted to change the gain of the amplifier such that the ambient light 13 was sufficient to allow absorption changes due to blood flow to be detected by the photodetector 5. The amplifier 7 was connected to a microprocessor which was configured to digitize the output signal 11 of the amplifier.

It can be seen from FIG. 5 that the data obtained from the photodetector 5 is almost binary in nature as the amplifier 7 saturates. The data obtained from the apparatus 1 is well synchronized with the more detailed data from the prior art PPG.

The comparison of the results also show that the pulse transit time (PTT) can be obtained by comparing an ECG measurement with the measurements obtained from the apparatus 1. In this case the apparatus 1 was attached to the wrist of the user so in the example of FIG. 5 the PTT gives the time it takes for the pulse to travel from the heart to the wrist.

Examples of the disclosure provide an apparatus 1 which may be used to monitor biometric parameters of a user. As the light collector 3 is configured to focus and filter light this means that the collected ambient light 13 may provide sufficient illumination to enable the changes in blood volume to be detected. This may enable the biometric parameters to be monitored without using any supplementary light sources 35 and so may reduce the power consumption of the apparatus 1. The apparatus 1 may be provided with one or more supplementary light sources 35 but these may be configured so that they are only activated when necessary. This enables the power consumption of the apparatus 1 to be minimized but also allows the apparatus 1 to be used at any time of day or night and in any light conditions.

The use of the sensitive photodetector 5 and amplifier 7 also enable the apparatus 1 to provide a useful output signal even if the amount of light scattered by the sample volume 17 is low.

As the apparatus 1 uses a minimal amount of power this reduces the power source needed for the apparatus 1 and enables the apparatus 1 to be used to monitor the biometric parameters for an extended period of time. Also as the apparatus 1 may only require a small amount of power this may enable the apparatus 1 to be small and light weight and may be more comfortable for a user to wear.

In some examples the light collector 3 may comprise a thin and flexible material. This may make the apparatus 1 thin and flexible so that the apparatus 1 is comfortable for a user to wear even for extended periods of time.

In the above description the term "coupled" means operationally coupled. Any number of intervening components may be provided including no intervening components.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed. For instance, in the examples described above the photodetector 5 is provided in the centre of a strap such as a wrist strap. In other examples the apparatus 1 may be configured so that the light collector 3 has radial symmetry about the photodetector 5.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising;
   a light collector configured to collect ambient light, increase an intensity of the ambient light collected, and provide the collected light to a portion of skin of a user;
   a photodetector configured to enable a biometric parameter to be monitored by detecting changes in the light absorbed by the portion of skin; and
   an amplifier configured to amplify an output signal provided by the photodetector;
   wherein the light collector comprises at least one waveguide patterned with a coupler microstructure configured to scatter the collected ambient light in the waveguide, the waveguide being configured to focus the collected ambient light onto the portion of the skin of the user and to filter the collected ambient light to increase the proportion of light within a selected range of wavelengths which is provided to the portion of skin of the user relative to the collected ambient light.

2. An apparatus as claimed in claim 1 wherein the waveguide comprises photoluminescent material configured to absorb light of a first wavelength and reemit light within the selected range of wavelengths.

3. An apparatus as claimed in claim 1 wherein the waveguide is configured to filter for different selected ranges of wavelengths to enable different biometric parameters to be monitored.

4. An apparatus as claimed in claim 1 wherein the waveguide is configured to provide light in one range of wavelengths selected to monitor heart rate.

5. An apparatus as claimed in claim 1 wherein the waveguide is configured to provide light in two different ranges of wavelengths selected to monitor blood oxygenation levels.

6. An apparatus as claimed in claim 1 wherein the apparatus comprises an array of photodetectors configured to enable a biometric parameter to be monitored by detecting changes in the light absorbed by the portion of skin.

7. An apparatus as claimed in claim 1 wherein the amplifier is configured to provide a variable gain.

8. An apparatus as claimed in claim 7 wherein the gain of the amplifier is dependent upon the intensity of the ambient light.

9. An apparatus as claimed in claim 1 further comprising a further photodetector configured to detect the brightness of the ambient light.

10. An apparatus as claimed in claim 1 wherein the apparatus comprises a supplementary light source.

11. An apparatus as claimed in claim 10 wherein the supplementary light source comprises one or more light emitting diodes.

12. An apparatus as claimed in claim 1 wherein the apparatus is configured so that the light collector and photodetector are positioned adjacent to the skin of the user.

13. An apparatus as claimed in claim 1 wherein the apparatus is configured to be worn by a user.

14. An apparatus as claimed in claim 1, wherein the waveguide is configured to filter using a filter that allows light within a selected range of wavelengths to pass through.

15. A method comprising;
    providing a light collector configured to collect ambient light, increase an intensity of the ambient light collected, and provide the collected light to a portion of skin of a user;
    providing a photodetector configured to enable a biometric parameter to be monitored by detecting changes in the light absorbed by the portion of skin; and
    providing an amplifier configured to amplify an output signal provided by the photodetector;
    wherein the light collector comprises at least one waveguide patterned with a coupler microstructure configured to scatter the collected ambient light in the waveguide, the waveguide being configured to focus the collected ambient light onto the portion of the skin of the user and to filter the collected ambient light to increase the proportion of light within a selected range of wavelengths which is provided to the portion of skin of the user relative to the collected ambient light.

16. A method as claimed in claim 15 wherein the waveguide comprises photoluminescent material configured to absorb light of a first wavelength and reemit light within the selected range of wavelengths.

17. A method as claimed in claim 15 wherein the light collector is configured to provide light in one range of wavelengths selected to enable a user's heart rate to be monitored.

18. A method as claimed in claim 15 wherein the light collector is configured to provide light in two different ranges of wavelengths to selected enable a user's blood oxygenation levels to be monitored.

19. A method as claimed in claim 15 wherein the amplifier is configured to provide a variable gain wherein the gain of the amplifier is dependent upon the intensity of the ambient light.

20. A method as claimed in claim 15 further comprising providing a supplementary light source wherein the supplementary light source comprises one or more light emitting diodes.

* * * * *